United States Patent [19]

Tsujihara et al.

[11] Patent Number: 5,767,094

[45] Date of Patent: Jun. 16, 1998

[54] PROPIOPHENONE DERIVATIVE AND PROCESSES FOR PREPARING THE SAME

[75] Inventors: Kenji Tsujihara, Urawa; Kunio Saito, Omiya; Mitsuya Hongu, Kawaguchi; Mamoru Matsumoto, Nara; Kozo Oka, Kyoto, all of Japan

[73] Assignee: Tanabe Seiyaku Co., Ltd., Osaka, Japan

[21] Appl. No.: 745,048

[22] Filed: Nov. 7, 1996

[30] Foreign Application Priority Data

Nov. 7, 1995 [JP] Japan .................................. 7-288487

[51] Int. Cl.⁶ .................... A01N 43/04; A01N 43/16; C07N 315/00; C07H 15/00
[52] U.S. Cl. .................... 514/25; 514/460; 514/866; 536/4.1; 536/18.2; 536/18.3; 536/18.5; 549/417; 549/418
[58] Field of Search ...................... 514/866, 460, 514/25; 549/418, 417; 536/4.1, 18.2, 18.3, 18.5

[56] References Cited

PUBLICATIONS

Bode et al. (1972) Biochim. Biophys. Acta, 290:134–149.
Abstract of J. Nutr. Sci. Vitaminol (1992) (Japan).
Fujiwara et al. (1988) Diabetes 37:1549–1558.
Szabo et al. (1982) Acta Alimentaria, vol. 11(1), pp. 31–37.

*Primary Examiner*—C. Warren Ivy
*Assistant Examiner*—Raymond Covington
*Attorney, Agent, or Firm*—Birch, Stewart, Kolasch & Birch, LLP

[57] ABSTRACT

A propiophenone derivative the formula [I]:

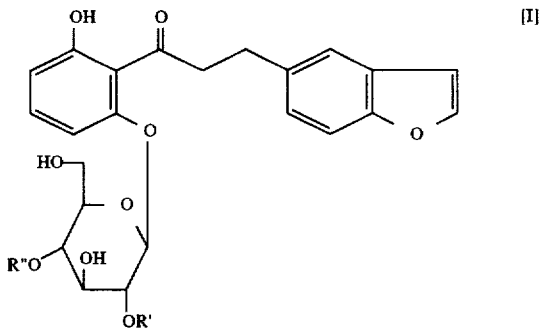

wherein R' is a lower alkanoyl group and R" is a hydrogen atom, or R' is a hydrogen atom and R" is a lower alkoxycarbonyl group, or a pharmaceutically acceptable salt thereof. Said compounds have excellent hypoglycemic activity so that they are useful in the prophylaxis or treatment of diabetes.

13 Claims, No Drawings

5,767,094

PROPIOPHENONE DERIVATIVE AND PROCESSES FOR PREPARING THE SAME

TECHNICAL FIELD

The present invention relates to a novel propiophenone derivative having a hypoglycemic activity, and processes for preparing the same.

PRIOR ART

Although diet therapy is essential in the treatment of diabetes, when diet therapy does not sufficiently control the conditions of patients, insulin or an oral antidiabetic is additionally used. There have been used as an antidiabetic biguanide compounds and sulfonylurea compounds. However, these antidiabetics have various side effects. For example, biguanide compounds cause lactic acidosis, and sulfonylurea compounds cause significant hypoglycemia. Under such circumstances, it has been desired to develop novel drugs for treatment of diabetes having no such side effects.

Recently, it has been reported that hyperglycemia participates in the outbreak and progressive impairment of diabetes, i.e. glucose toxicity theory. That is, chronic hyperglycemia leads to decrease insulin secretion and contributes to increase insulin resistance, and as a result, the blood glucose concentration is increased so that diabetes is self-exacerbated [cf. Diabetologia, Vol. 28, p. 119 (1985); Diabetes Care, Vol. 13, p. 610 (1990), etc.]. Thus, by treating hyperglycemia, the aforementioned self-exacerbating cycle is interrupted so that the prophylaxis or treatment of diabetes is made possible.

As one of the methods for treating hyperglycemia, it is considered to excrete an excess amount of glucose directly into urine so that the blood glucose concentration is normalized.

Phlorizin is a glycoside which exists in barks and stems of Rosaceae (e.g., apple, pear, etc.). Recently, it has been found that phlorizin is an inhibitor of $Na^+$-glucose co-transporter which exists only at chorionic membrane of the intestine and the kidney, by which phlorizin inhibits the renal tubular glucose reabsorption and promotes the excretion of glucose so that the blood glucose is controlled. Based on this action of phlorizin, when the blood glucose concentration in diabetic animals is controlled at a normal level for a long time by subcutaneous daily administration of phlorizin but without using insulin, the conditions of diabetic animals are ameliorated to be normal [cf. Journal of Clinical Investigation, Vol. 79, p. 1510 (1987), ibid. Vol. 80, p. 1037 (1987), ibid. Vol. 87, p. 561 (1991), etc.].

However, when phlorizin is administered orally, most of it is hydrolyzed into glucose and phloretin, which is the aglycon of phlorizin, and hence, the amount of phlorizin to be absorbed is so little that the urine glucose excretion effect of phlorizin is very weak. Besides, phloretin, which is the aglycon of phlorizin, has been known to inhibit strongly a facilitated diffusion-type glucose transporter, for example, when phloretin is intravenously administered to rats, the glucose concentration in brain of rats is decreased [cf. Stroke, Vol. 14, p. 388 (1983)]. Thus, when phlorizin is administered for a long time, there may be bad effects on various tissues, and hence, phlorizin has not been used as an antidiabetic.

BRIEF DESCRIPTION OF INVENTION

An object of the present invention is to provide a propiophenone derivative which inhibits the renal tubular glucose reabsorption by which it shows an urine glucose increasing activity, and shows an excellent hypoglycemic activity, and further an aglycon thereof has a very weak inhibitory activity of facilitated diffusion-type glucose transporter. Another object of the present invention is to provide a hypoglycemic agent comprising as an active ingredient a propiophenone derivative of the present invention or a pharmaceutically acceptable salt thereof. A further object of the present invention is to provide a process for preparing a propiophenone derivative of the present invention.

DETAILED DESCRIPTION OF INVENTION

The present Invention relates to a propiophenone derivative of the formula [I]:

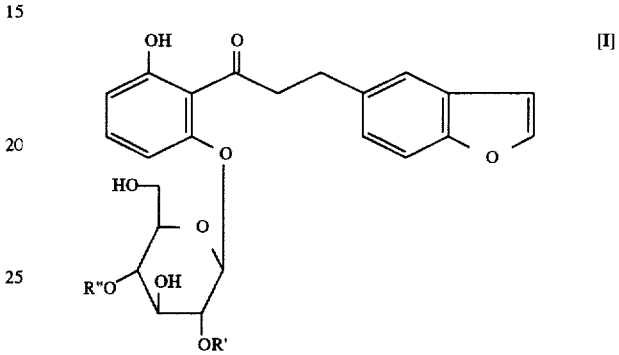

wherein R' is a lower alkanoyl group, and R" is a hydrogen atom, or R' is a hydrogen atom, and R" is a lower alkoxycarbonyl group, or a pharmaceutically acceptable salt thereof.

The propiophenone derivatives [I] of the present invention may be used for the purpose of the present invention either in the free form or in the form of a pharmaceutically acceptable salt thereof. The pharmaceutically acceptable salt may be an alkali metal salt, etc.

The compounds [I] of the present invention or a pharmaceutically acceptable salt thereof may be administered either orally or parenterally, or may be formulated into a pharmaceutical preparation in admixture with a pharmaceutically acceptable carrier or diluent suitable for oral administration or parenteral administration. The pharmaceutically acceptable carrier or diluent may be, for example, binders (e.g., syrup, gum arabic, gelatin, sorbitol, tragacanth, polyvinylpyrrolidone, etc.), excipients (e.g., lactose, sucrose, corn starch, potassium phosphate, sorbitol, glycine, etc.), lubricants (e.g., magnesium stearate, talc, polyethylene glycol, silica, etc.), disintegrators (e.g., potato starch, etc.), wetting agents (e.g., sodium laurylsulfate, etc.), and the like. These pharmaceutical preparations may be in the form of a solid preparation such as tablets, capsules, powders, granules, etc., or in the form of a liquid preparation such as solution, suspension, emulsion, etc., when administered orally. When administered parenterally, the pharmaceutical preparations may be in the form of an injection preparation or an intravenous drip preparation using distilled water for injection, a biological saline solution, an aqueous glucose solution, etc.

The dose of the present compound [I] varies depending on ages, weights and conditions of patients, or severity of diseases to be cured, but it may be in the range of 0.1 to 500 mg/kg/day, preferably in the range of 1 to 50 mg/kg/day in case of oral administration. In case of parenteral administration, the dose of the present compound [I] may be in the range of 0.01 to 50 mg/kg/day, preferably in the range of 0.1 to 10 mg/kg/day.

The compound [I] of the present invention, wherein R' is a lower alkanoyl group, and R" is a hydrogen atom, i.e., the compound of the formula [I-a]:

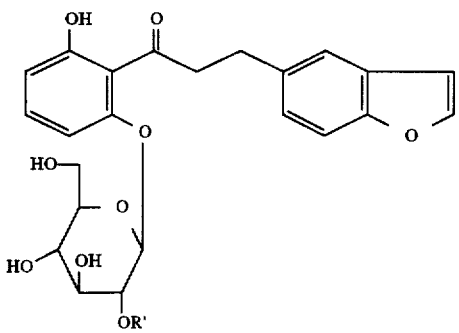

wherein R' is a lower alkanoyl group, or a pharmaceutically acceptable salt thereof, may be prepared by reacting a propiophenone derivative of the formula [II]:

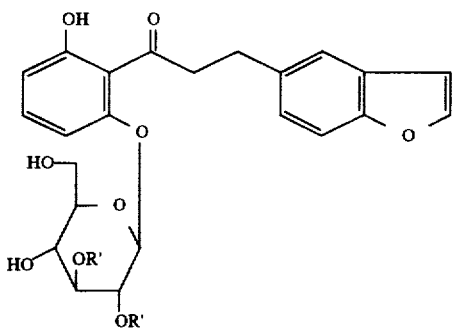

wherein R' is a lower alkanoyl group, with an alkanesulfonic acid or an arylsulfonic acid, and if desired, converting the product into a pharmaceutically acceptable salt thereof.

The above reaction may be carried out in a suitable organic solvent, at a temperature from a room temperature to with heating, preferably at a temperature from room temperature to 50° C. The organic solvent may be any one which does not affect the reaction, for example, methanol, ethanol, etc. The alkanesulfonic acids and arylsulfonic acids may include methanesulfonic acid, ethanesulfonic acid, benzenesulfonic acid, p-toluenesulfonic acid, etc., which are usually used in an amount of 0.05 mole to 0.2 mole equivalent, to 1 mole of the starting compound [II].

The compound [I] of the present invention, wherein R' is a hydrogen atom, and R" is a lower alkoxycarbonyl group, i.e., the compound of the formula [I-b]:

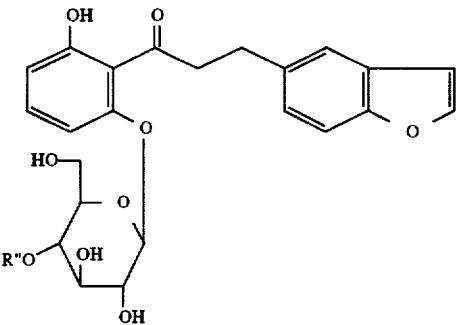

wherein R" is a lower alkoxycarbonyl group, or a pharmaceutically acceptable salt thereof, may be prepared by reacting a propiophenone derivative of the formula [III]:

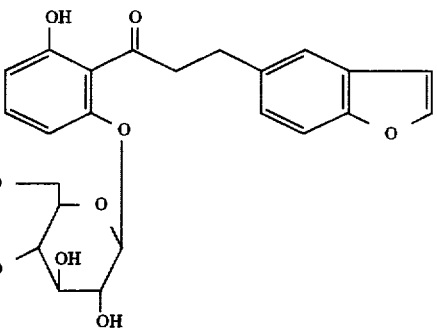

with a lower alkanol and an alkanesulfonic acid or an arylsulfonic acid, and if desired, converting the product into a pharmaceutically acceptable salt thereof.

The lower alkanol used in the above reaction may be a straight chain or branched chain alkanol having 1 to 6 carbon atoms, for example, methanol, ethanol, propanol, isopropanol, n-butanol, tert-butanol, etc., and may be used in an equimolar amount or a little excess amount to 1 mole of the starting compound [III]. The same alkanesulfonic acids and arylsulfonic acids as described above may be used in the reaction.

In this reaction, a lower alkanol which is used as a reagent may also serve as solvent, but the other organic solvent which does not affect the reaction may be used. This reaction may be carried out usually at a temperature from a room temperature to with heating.

The starting compound [II] used in the present invention may be prepared according to the following steps.

(1) First, the acetophenone compound of the formula [IV]:

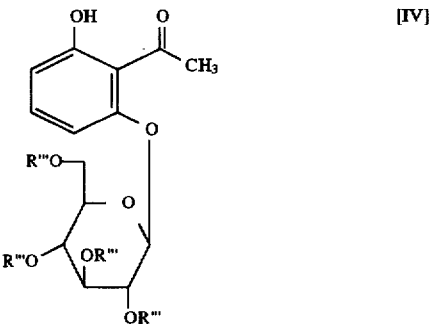

wherein R''' is a hydrogen atom or a protecting group for a hydroxy group, is condensed with an aldehyde compound of the formula [V]:

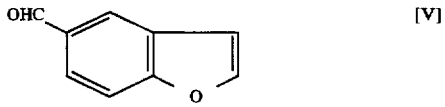

followed by removal of the protecting groups to give the acrylophenone derivative of the formula [VI]:

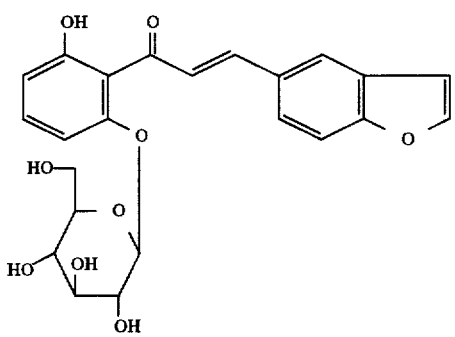

(2) The above acrylophenone derivative [VI] is reduced to give the compound of the formula [VII]:

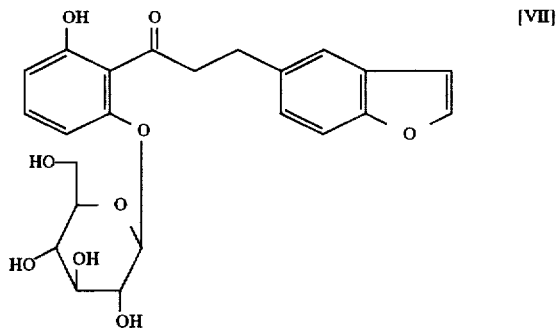

(3) The 4- and 6-hydroxy groups of the β-D-glucopyranosyl group of the above compound [VII] are protected to give the compound of the formula [VIII]:

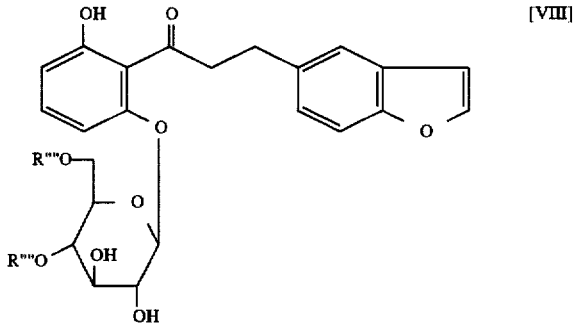

wherein R"" is the protecting group for a hydroxy group, and the 2- and 3-hydroxy groups of the β-D-glucopyranosyl group are acylated with lower alkanoyl groups, then followed by removal the protecting groups.

The condensation reaction of the acetophenone derivative [IV] with the aldehyde compound [V], in the step (1) described above, may be carried out by the conventional method, for example, in a solvent (an organic solvent such as methanol, ethanol, etc. or a mixture of these organic solvents and water), in the presence of a base (alkali metal hydroxides, etc.), from a temperature under cooling to a temperature with heating (especially at a temperature between 10° C. and 30° C.).

The protecting groups for the hydroxy groups in the acetophenone derivative [IV] may be any conventional protecting groups, for example, alkanoyl groups such as acetyl group, etc., aralkyl groups such as benzyl group, etc.

The reduction reaction of the acrylophenone derivative [VI], in the step (2) described above, may be carried out by a conventional method such as reduction with a metal hydride, catalytic reduction, etc. For example, the reduction with a metal hydride may be carried out by using a metal hydride in a solvent, and the catalytic reduction may be carried out by using a catalyst under atmospheric pressure of hydrogen gas in a solvent.

In the catalytic reduction, the catalyst may be any conventional one, for example, palladium-carbon, platinum-carbon, platinum oxide, etc.

In the reduction with a metal hydride, the metal hydride may be any one which can reduce a double bond. However, it may be preferable to use metal hydrides which do not reduce a ketone, for example, sodium tellurium hydride (NaTeH), which is prepared according to the method disclosed in Synthesis, p. 545 (1978). Sodium tellurium hydride is usually used in an amount of 1 to 3 mole equivalents, preferably in an amount of 1 to 1.5 mole equivalents, to 1 mole equivalent of the compound [VI].

In the above reduction reaction, the solvent may be any one which does not affect the reaction, for example, an organic solvent such as methanol, ethanol, tetrahydrofuran, ethyl acetate, acetic acid, etc., or a mixture of these organic solvents and water.

This reduction reaction may be carried out from a temperature under cooling to a temperature with heating, preferably at a temperature from 10° C. to 30° C.

The protecting groups for the 4- and 6-hydroxy groups of the β-D-glucopyranosyl group of the compound [VIII] in the step (3) may be any conventional one. However, it is preferable to use the benzylidene group or alkylidene groups such as isopropylidene group, etc., which are formed by combining these two protecting groups for the 4- and 6-hydroxy groups with each other.

The acylation of the compound [VIII] with a lower alkanoyl group in the step (3) may be carried out by reacting an alkylcarboxylic acid corresponding to the desired alkanoyl group, a salt thereof, or a reactive derivative thereof (hereafter these groups being referred to as alkanoylating agent), with the compound [VIII].

The reaction of an alkylcarboxylic acid compound or a salt thereof with the compound [VIII] may be carried out in the presence or absence of a condensing agent in a suitable solvent. The reaction of a reactive derivative of the alkylcarboxylic acid compound with the compound [VIII] may be carried out in the presence or absence of an acid acceptor in a suitable solvent or without a solvent.

The salt of an alkylcarboxylic acid may be, for example, an alkali metal salt or alkaline earth metal salt such as sodium salt, potassium salt, calcium salt, etc. When a salt of an alkylcarboxylic acid is used in the condensation reaction, the salt is preferably used in the reaction after the conversion thereof into a free acid.

The reactive derivative of an alkylcarboxylic acid may be, for example, an acid halide, an acid anhydride or an active ester of the corresponding alkylcarboxlic acids.

The condensing agent may be any conventional one, for example, dicyclohexylcarbodiimide, diethyl cyanophosphate, carbonyldiimidazole, N,N-bis(2-oxo-3-oxazolidinyl)phosphinic chloride, etc.

The acid acceptor may be any conventional one, for example, an inorganic base such as an alkali metal hydroxide (e.g. sodium hydroxide, potassium hydroxide, etc.); an alkali metal carbonate (e.g. sodium carbonate, potassium carbonate, etc.); an alkali metal hydrogen carbonate (e.g. sodium hydrogen carbonate, potassium hydrogen carbonate, etc.); an alkali metal hydride (e.g. sodium hydride, potassium hydride, etc.), or an organic base such as a tri-lower alkylamine (e.g., triethylamine, diisopropylethylamine, etc.); pyridine; dimethylaminopyridine; aniline; dimethylaniline, etc.

7

The solvent may be any conventional one which does not affect the reaction, for example, dichloromethane, dimethylformamide, tetrahydrofuran, acetonitrile, pyridine, etc.

The reaction may be carried out from a temperature under cooling to a temperature with heating, preferably at a temperature from −10° C. to 100° C., especially at a temperature from 0° C. to 50° C.

The removal of the lower alkanoyl groups from the lower-alkanolyated phenolic hydroxy groups may be carried out by treating the compound with a base in a suitable solvent.

The base may be any conventional one, for example, an alkali metal hydrogen carbonate such as sodium hydrogen carbonate, potassium hydrogen carbonate, etc. The solvent may be any conventional one which does not affect the reaction, for example, tetrahydroduran, methanol, water, etc.

The reaction may be carried out with heating, preferably at a temperature from 25° C. to 60° C., especially at a temperature from 25° C. to 40° C.

The removal of the protecting groups for the 4- and 6-hydroxy groups of the β-D-glucopyranosyl group may be carried out in aqueous acetic acid in the presence of an alkanesulfonic acid or an arylsulfonic acid. The alkanesulfonic acid and arylsulfonic acid may be the ones described above. The reaction may preferably be carried out at room temperature.

The other starting compound [III] is prepared by reacting the aryl halogenoformate such as p-nitrophenyl chloroformate, etc. or carbonyldiimidazole, etc., with the above intermediate [VII].

The above reaction is carried out in a suitable organic solvent such as 2,4,6-collidine, 2,6-lutidine, pyridine, tetrahydrofuran, etc., from a temperature under cooling to a room temperature.

The acetophenone derivative [IV] used for preparation of the above starting compound [II] may be prepared (i) according to a method disclosed in Journal of Medicinal and Pharmaceutical Chemistry, Vol. 5, p. 1054 (1962), for example, by reacting 2',6'-dihydroxyacetophenone with 2,3,4,6-tetra-O-acetyl-α-D-glucopyranosyl bromide in the presence of potassium hydroxide in aqueous acetone, or (ii) for example, refluxing 2',6'-dihydroxyacetophenone and 2,3,4,6-tetra-O-acetyl-α-D-glucopyranosyl bromide in the presence of cadmium carbonate in toluene.

In the present invention, the lower alkanoyl group means a straight chain or branched chain alkanoyl group having 2 to 7 carbon atoms, for example, acetyl group, propionyl group, butyryl group, 2-methylpropionyl group, valeryl group, etc., preferably the ones having 2 to 5 carbon atoms. The lower alkoxycarbonyl group means an alkoxycarbonyl group wherein the alkoxy moiety is a straight chain or branched chain alkoxy group having 1 to 6 carbon atoms, preferably ones having 1 to 4 carbon atoms, for example, methoxycarbonyl group, ethoxycarbonyl group, propoxycarbonyl group, isopropoxycarbonyl group, butoxycarbonyl group, isobutoxycarbonyl group, tert-butoxycarbonyl group, etc.

EXAMPLES

The following Examples and Reference Examples are the concrete explanation of the present invention, but the present invention should not be limited thereto.

Example 1

2'-(2,3-di-O-Acetyl-β-D-glucopyranosyloxy)-6'-hydroxy-3-(5-benzo[b]-furanyl)propiophenone (1000 mg) is dissolved in methanol (10 ml), and thereto is added p-toluenesulfonic acid (36 mg). The mixture is stirred at 40° C. for 22.5 hours. After cooling, to the reaction solution are added ethyl acetate and a saturated aqueous sodium hydrogen carbonate solution, and the organic layer is obtained by separation, dried, and evaporated to remove the solvent. The resulting residue is purified by silica gel column chromatography (solvent; chloroform-methanol) to give 2'-(2-O-acetyl-β-D-glucopyranosyloxy)-6'-hydroxy-3-(5-benzo[b]furanyl)propiophenone (373 mg).

m.p. 152°–156° C. ESI-MS (m/z): 509 [(M+Na)$^+$]IR (nujol) cm$^{-1}$: 3450, 3350, 1750, 1630 NMR (DMSO-d$_6$) δ:1.98 (3H, s), 2.8–3.1 (4H, m), 3.26 (1H, m), 3.4–3.6 (3H, m), 3.72 (1H, dd, J=5.3, 10.2 Hz), 4.67 (1 H, t, J=5.6 Hz), 4.76 (1H, dd, J=8.2, 9.5 Hz), 5.12 (1H, d, J=8.1 Hz), 5.27 (1H, d, J=5.4 Hz), 5.36 (1H, d, J=5.5 Hz), 6.55 (1H, d, J=8.1 Hz), 6.66 (1H, d, J=8.4 Hz), 6.88 (1H, dd, J=0.9, 2.2 Hz), 7.17 (1H, t, J=8.5 Hz), 7.19 (1H, dd, J=2.0, 8.5 Hz), 7.48 (1H, d, J=8.5 Hz), 7.51 (1H, d, J=1.6 Hz), 7.93 (1H, d, J=2.2 Hz), 10.24 (1H, s)

Example 2

2'-(4,6-O-Oxomethylene-β-D-glucopyranosyloxy)-6'-hydroxy-3-(5-benzo[b]furanyl)propiophenone (794 mg) is dissolved in methanol (20 ml), and thereto is added p-toluenesulfonic acid (32 mg). The mixture is stirred at room temperature for 2 hours. To the reaction solution are added ethyl acetate and a saturated aqueous sodium hydrogen carbonate solution, and the organic layer is obtained by separation, dried, and evaporated to remove the solvent. The resulting residue is purified by silica gel column chromatography (solvent; chloroform-methanol) to give 2'-(4-O-methoxycarbonyl-β-D-glucopyranosyloxy)-6'-hydroxy-3-(5-benzo[b]furanyl)propiophenone (391 mg) as pale yellow foam.

ESI-MS (m/z): 525 [(M+Na)$^+$] IR (nujol) cm$^{-1}$: 3420, 1750,1625 NMR (DMSO-d$_6$) δ: 3.00 (2H, t, J=7.5 Hz), 3.2–3.6 (6H, m), 3.66 (1H, m), 3.72 (3H, s), 4.51 (1H, t, J=9.5 Hz), 4.79 (1H, t, J=5.5 Hz), 5.06 (1H, d, J=8.1 Hz), 5.51 (1H, d, J=5.9 Hz), 5.57 (1H, d, J=5.9 Hz), 6.56 (1H, d, J=8.1 Hz), 6.69 (1H, d, J=8.1 Hz), 6.89 (1H, dd, J=0.7, 2.2 Hz), 7.21 (1H, dd, J=1.8, 8.4 Hz), 7.24 (1H, t, J=8.4 Hz), 7.47 (1H, d, J=8.4 Hz), 7.53 (1H, d, J=1.5 Hz), 7.93 (1H, d, J=2.2 Hz), 10.89 (1H, s)

Reference Example 1

(1) To a mixture of 2'-(2,3,4,6-tetra-O-acetyl-β-D-glucopyranosyloxy)-6'-hydroxyacetophenone (965 mg), benzo[b]furan-5-carbaldehyde (350 mg) and ethanol (10 ml) is added dropwise a 50% aqueous potassium hydroxide solution (2 ml), and the mixture is stirred at room temperature overnight. The mixture is evaporated to remove the solvent under reduced pressure, and to the residue are added water and diisopropyl ether. The mixture is stirred, and the aqueous layer is obtained by separation. The aqueous layer is neutralized by using a 10% hydrochloric acid under ice-cooling, and extracted with ethyl acetate. The resulting organic layer is washed with water, dried, and evaporated to remove the solvent to give crude 2'-(β-D-glucopyranosyloxy)-6'-hydroxy-3-(5-benzo[b]furanyl)acrylophenone.

(2) The product thus obtained is added to a solution of sodium tellurium hydride in ethanol (15 ml), which is previously prepared from tellurium (383 mg) and sodium borohydride (270 mg), and the mixture is reacted at room temperature for 2.5 hours. The insoluble materials are removed by filtration, and to the filtrate are added water and ethyl acetate. The mixture is stirred, and the organic layer is obtained by separation, washed with water, dried, and evaporated to remove the solvent. The residue is purified by silica gel column chromatography to give 2'-(β-D-glucopyranosyloxy)-6'-hydroxy-3-(5-benzo[b]-furanyl) propiophenone (480 mg).

(3) To a mixture of the product obtained in the above (2) (444 mg) and dichloromethane (8 ml) are added benzaldehyde dimethyl acetal (304 mg) and p-toluenesulfonic acid (19 mg), and the mixture is stirred at room temperature for two hours. The mixture is evaporated to remove the solvent under reduced pressure, and the resulting residue is dissolved in ethyl acetate. The organic layer is washed with water, dried, and evaporated to remove the solvent. The residue is purified by silica gel column chromatography (solvent; chloroform-methanol) to give 2'-(4,6-O-benzylidene-β-D-glucopyranosyloxy)-6'-hydroxy-3-(5-benzo[b]furanyl)propiophenone (584 mg).

(4) The product obtained in the above (3) (578 mg) is dissolved in pyridine (5 ml), and thereto is added acetic anhydride (665 mg). The mixture is stirred at room temperature for four hours. To the reaction solution is added ethyl acetate, and the mixture is poured into a mixture of ice-10% hydrochloric acid. The mixture is stirred, and the organic layer is obtained by separation, washed with water, dried, and evaporated to remove the solvent to give crude 2'-(2,3-di-O-acetyl-4,6-O-benzylidene-β-D-glucopyranosyloxy)-6'-acetoxy-3-(5-benzo-[b]furanyl) propiophenone (724 mg).

(5) The product obtained in the above (4) (720 mg) is dissolved in a mixture of tetrahydrofuran-methanol (10 ml-10 ml), and thereto are added sodium hydrogen carbonate (428 mg) and water (0.1 ml), and the mixture is stirred at 50° C. for 6.5 hours. Residual sodium hydrogen carbonate is removed by filtration, and the filtrate is concentrated under reduced pressure. The resulting residue is dissolved in ethyl acetate, and the solution is washed with water, dried, and evaporated to remove the solvent. The residue is purified by silica gel column chromatography (solvent; chloroform-ethyl acetate) to give 2'-(2,3-di-O-acetyl-4,6-O-benzylidene-β-D-glucopyranosyloxy)-6'-hydroxy-3-(5-benzo[b]furanyl)propiophenone (520 mg).

(6) The product obtained in the above (5) (121 mg) is dissolved in acetic acid (5 ml), and thereto are added water (0.5 ml) and p-toluenesulfonic acid (5 mg). The mixture is stirred at room temperature for 4.5 hours, and thereto are added water and ethyl acetate. The mixture is stirred, and the organic layer is obtained by separation, washed with water, dried, and evaporated to remove the solvent. The resulting residue is purified by silica gel column chromatography (solvent; chloroform-methanol) to give 2'-(2,3-di-O-acetyl-β-D-glucopyranosyloxy)-6'-hydroxy-3-(5-benzo[b]furanyl) propiophenone (91.5 mg).

m.p. 127°–129° C. FABMS (m/z): 551 [(M+Na)$^+$] NMR (DMSO-d$_6$) δ:1.92 (3H, s), 2.00 (3H, s), 2.85–3.05 (4H, m), 3.45–3.75 (4H, m), 4.75 (1H, t, J=5.4 Hz), 4.87 (1H, dd, J=8.0, 9.8 Hz), 5.09 (1H, t, J=9.7 Hz), 5.36 (1H, d, J=7.9 Hz), 5.55 (1H, d, J=5.6 Hz), 6.57 (1H, d, J=7.8 Hz), 6.68 (1H, d, J=8.1 Hz), 6.88 (1H, d, J=2.2 Hz), 7.17 (1H, d, J=9.6 Hz), 7.19 (1H, t, J=8.3 Hz), 7.48 (1H, d, J=9.3 Hz), 7.49 (1H, d, J=1.0 Hz), 7.93 (1H, d, J=2.2 Hz), 10.28 (1H, s)

Reference Example 2

2'-(β-D-Glucopyranosyloxy)-6'-hydroxy-3-(5-benzo[b] furanyl)-propiophenone (1333 mg) is dissolved in 2,4,6-collidine (15 ml). The solution is chilled to −40° C. with dry ice-acetone, and thereto is added dropwise a solution of p-nitrophenyl chloroformate (786 mg) in methylene chloride (3 ml) under stirring. The solution is stirred at −40° C. for 1 hour and 45 minutes, subsequently stirred at room temperature for one hour, and further stirred at 50° C. for 6.5 hours. After cooling, the reaction solution is poured into cold 10% hydrochloric acid, and extracted with ethyl acetate. The organic layer is washed with water, dried, and evaporated to remove the solvent. The residue is purified by silica gel column chromatography (solvent; chloroform-acetone) to give 2'-(4,6-O-oxomethylene-β-D-glucopyranosyloxy)-6'-hydroxy-3-(5-benzo[b]furanyl)propiophenone (994 mg).

m.p. 70° C. −(slowly decomposed) FAB-MS (m/z): 493 [(M+Na)$^+$] IR (nujol) cm$^{-1}$: 3400, 1750, 1620 NMR (DMSO-d$_6$) δ: 2.98 (2H, t, J=7.5 Hz), 3.23 (2H, m), 3.33 (1H, m), 3.63 (1H, m), 4.13 (1H, m), 4.17 (1H, dd, J=8.9, 9.5 Hz), 4.25 (1H, dd, J=9.5, 9.6 Hz), 4.47 (1H, dd, J=5.5, 9.2 Hz), 5.21 (1H, d, J=7.9 Hz), 5.77 (1H, d, J=5.9 Hz), 5.84 (1H, d, J=5.5 Hz), 6.58 (1H, d, J=8.1 Hz), 6.68 (1H, d, J=8.1 Hz), 6.88 (1H, dd, J=0.9, 2.2 Hz), 7.19 (1H, dd, J=1.8, 8.5 Hz), 7.24 (1H, t, J=8.3 Hz), 7.48 (1H, d, J=8.5 Hz), 7.50 (1H, d, J=1.8 Hz), 7.93 (1H, d, J=2.2 Hz), 10.73 (1H, s)

Effects of the Invention

The compounds [I] of the present invention and the pharmaceutically acceptable salts thereof have an excellent hypoglycemic activity. For example, when administered orally to rats, the present compounds described in Examples increased the amount of urine glucose more than 50 times as much as phlorizin did.

In addition, the compounds [I] have low toxicity. Besides, the aglycones of the compounds [I], the hydrolysates thereof, show extremely a weak inhibitory activity against facilitated diffusion-type glucose transporter.

Therefor, the compounds [I] of the present invention can treat hyperglycemia, by which the self-exacerbating cycle of glucose toxicity is interrupted, so that the compounds [I] are useful in the prophylaxis or treatment of diabetes [e.g., diabetes mellitus such as insulin-dependent diabetes (I-type diabetes), insulin-independent diabetes (II-type diabetes)].

What is claimed is:

1. A propiophenone derivative of the formula [I]:

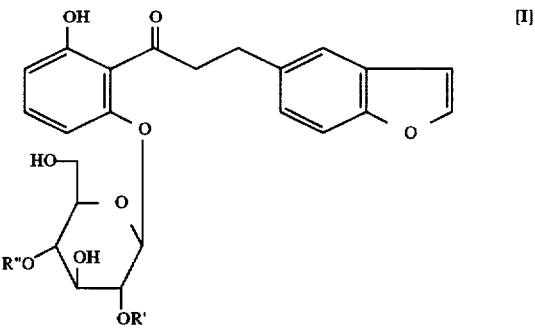

wherein R' is a lower alkanoyl group, and R" is a hydrogen atom, or R' is a hydrogen atom, and R" is a lower alkoxycarbonyl group, or a pharmaceutically acceptable salt thereof.

2. The compound according to claim 1, wherein R' is a lower alkanoyl group, and R" is a hydrogen atom.

3. The compound according to claim 1, wherein R' is a hydrogen atom, and R" is a lower alkoxycarbonyl group.

4. A process for preparing a propiophenone derivative of the formula [I-a]:

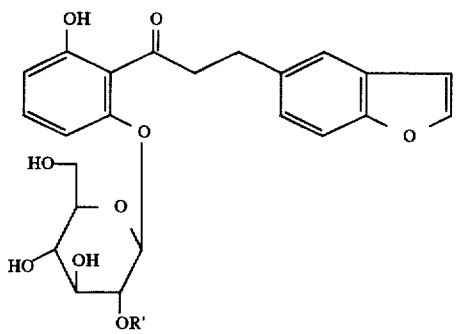

[I-a]

wherein R' is a lower alkanoyl group, or a pharmaceutically acceptable salt thereof, which comprises reacting a propiophenone compound of the formula [II]:

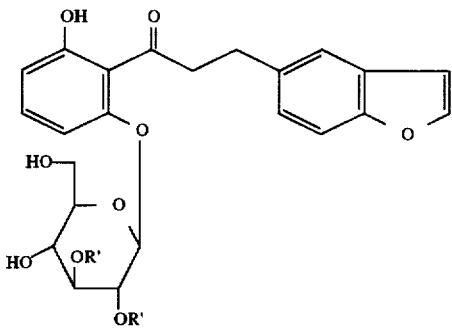

[II]

wherein R' is the same as defined above, with an alkanesulfonic acid or an arylsulfonic acid, and if desired, converting the product into a pharmaceutically acceptable salt thereof.

5. A process for preparing a propiophenone derivative of the formula [I-b]:

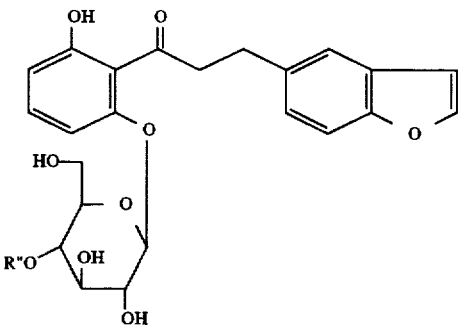

[I-b]

wherein R" is a lower alkoxycarbonyl group, or a pharmaceutically acceptable salt thereof, which comprises reacting a propiophenone compound of the formula [III]:

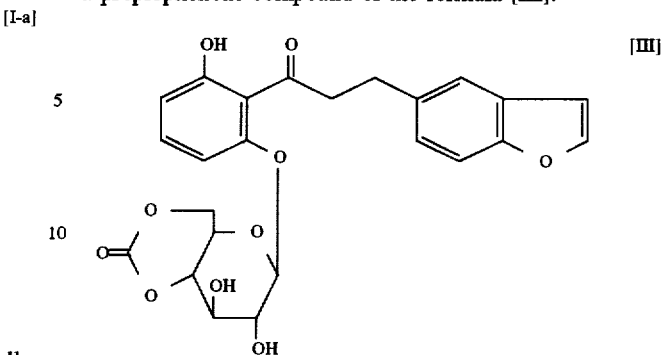

[III]

with a lower alkanol and an alkanesulfonic acid or an arylsulfonic acid, and if desired, converting the product into a pharmaceutically acceptable salt thereof.

6. A pharmaceutical composition which comprises a therapeutically effective amount of the compound as set forth in claim 1 in admixture with a pharmaceutically acceptable carrier or diluent.

7. A method for prophylaxis or treatment of diabetes in a patient, which comprises administering to said patient a therapeutically effective amount of the compound as set forth in claim 1.

8. The compound 2'-(2-O-Acetyl-β-D-glucopyranosyloxy)-6'-hydroxy-3-(5-benzo[b]-furanyl) propiophenone.

9. The compound 2'-(4-O-methoxycarbonyl-β-D-glucopyranosyloxy)-6'-hydroxy-3-(5-benzo[b]furanyl) propiophenone.

10. A pharmaceutical composition which comprises a therapeutically effective amount of the compound as set forth in claim 8 in admixture with a pharmaceutically acceptable carrier or diluent.

11. A method for prophylaxis or treatment of diabetes in a patient, which comprises administering to said patient a therapeutically effective amount of the compound as set forth in claim 8.

12. A pharmaceutical composition which comprises a therapeutically effective amount of the compound as set forth in claim 9 in admixture with a pharmaceutically acceptable carrier or diluent.

13. A method for prophylaxis or treatment of diabetes in a patient, which comprises administering to said patient a therapeutically effective amount of the compound as set forth in claim 9.

* * * * *